(12) United States Patent
Mace et al.

(10) Patent No.: US 11,464,249 B2
(45) Date of Patent: Oct. 11, 2022

(54) NUTRITIONAL COMPOSITION

(71) Applicant: SOCIÉTÉ DES PRODUITS NESTLÉ S.A., Vevey (CH)

(72) Inventors: Catherine Mace, Conversion (CH); Magalie Sabatier, Lausanne (CH); Yassaman Shahkhalili Dulloo, La Tour de Peilz (CH); Carmen Tudorica, Vevey (CH)

(73) Assignee: Societe des Produits Nestle S.A., Vevey (CH)

( * ) Notice: Subject to any disclaimer, the term of this patent is extended or adjusted under 35 U.S.C. 154(b) by 467 days.

(21) Appl. No.: 16/406,235

(22) Filed: May 8, 2019

(65) Prior Publication Data

US 2020/0008452 A1 Jan. 9, 2020

(51) Int. Cl.

| A61K 36/00 | (2006.01) |
| A23L 11/00 | (2021.01) |
| A23L 33/165 | (2016.01) |
| A23L 7/10 | (2016.01) |
| A23L 33/00 | (2016.01) |
| A23L 33/105 | (2016.01) |
| A61K 31/6615 | (2006.01) |
| A61K 36/48 | (2006.01) |

(52) U.S. Cl.
CPC .............. *A23L 11/01* (2016.08); *A23L 7/10* (2016.08); *A23L 7/101* (2016.08); *A23L 7/197* (2016.08); *A23L 11/05* (2016.08); *A23L 33/105* (2016.08); *A23L 33/165* (2016.08); *A23L 33/40* (2016.08); *A61K 31/6615* (2013.01); *A61K 36/48* (2013.01); *A23V 2002/00* (2013.01)

(58) Field of Classification Search
CPC ................................ A23L 7/115; A23L 7/197
See application file for complete search history.

(56) References Cited

U.S. PATENT DOCUMENTS

| 2011/0293790 A1 | 12/2011 | Ewing |
| 2014/0030241 A1 | 1/2014 | Greenberg |
| 2016/0128367 A1 | 5/2016 | Huntsman |

FOREIGN PATENT DOCUMENTS

| BG | 106828 A | 1/2004 | |
| CN | 103844196 | 6/2014 | |
| CN | 106106759 A | 11/2016 | |
| DE | 102014016279 | 5/2016 | |
| EP | 1121860 A1 * | 8/2001 | ............. A21D 13/40 |
| FR | 323398 | 3/1903 | |
| IN | 2009MU01935 | 2/2012 | |
| IN | 2012MU00439 | 11/2013 | |
| WO | 2008090545 | 7/2008 | |
| WO | 2011151096 | 12/2011 | |
| WO | 2012033812 | 3/2012 | |
| WO | 2016050578 | 4/2016 | |
| WO | 2016075595 | 5/2016 | |
| WO | 2017080498 | 5/2017 | |
| WO | 2017178395 | 10/2017 | |

OTHER PUBLICATIONS

DellaValle et al, Differences in relative iron bioavailability in traditional Bangladeshi meal plans. Food and Nutrition Bulletin (2014), vol. 35, No. 4, pp. 431-439. (Year: 2014).*
Podder et al, Iron fortification of lentil (*Lens culinaris* Medik.) to address iron deficiency). Podder et al teach Nutrients (2017), vol. 9, No. 8, 863 (Year: 2017).*
Podder et al, Relative bioavailability of iron in Bangladeshi traditional meals prepared with iron-fortified lentil dal. Nutrients (2018), vol. 10, No. 3, 354 p (Year: 2018).*
Feosol, "About Iron", Retrieved from http://www.feosol.com/about-iron/, Oct. 1, 2016, 7 Pages.
Ngan, "Iron Deficiency", DermNet NZ, Retrieved from https://dermnetnz.org/topics/iron-deficiency/, 2005, pp. 1-7.
Della Valle et al., "Differences in Relative Iron Bioavailability in Traditional Bangladeshi Meal Plans", Food and Nutrition Bulletin, vol. 35, Issue No. 4, Dec. 22, 2014, pp. 431-439.
Wang, "Pharmacology", 1st Edition, Jun. 30, 2016, p. 184.
China Patent Office Communication for Application No. 201980036828.3, dated Jul. 20, 2021, 10 Pages.
International Search Report to PCT/IB2019/053789 dated Jul. 17, 2019.
GLahn et al, Caco-2 Cell Ferritin Formation Predicts Nonradiolabeled Food Iron Availability in an In Vitro Digestion/Caco-2 Cell Culture Model, American Society for Nutritional Sciences, 1998, pp. 1555-1561.
Podder et al, Iron Fortification of Lentil (*Lens culinaris* Medik.) to Address Iron Deficiency, MDPI Journal, Nutrients 2017, pp. 1-12.
Weinborn, et al, The Effect of Plant Proteins Derived from Cereals and Legumes on Heme Iron Absorption, MDPI Journal, Nutrients 2015, pp. 8977-8986.
Della Valle, et al, Iron Absorption from an Intrinsically Labeled Lentil Meal Is Low but Upregulated in Women with Poor Iron Status, The Journal of Nutrition, 2015, pp. 2253-2257.
Villarroel et al, Effect of dietary protein on heme iron uptake by Caco-2 cells, Eur J Nutr. 2011, pp. 637-643.
Rewashdeh et al, Iron Bioavailability of rats fed liver, lentil, spinach and their mixtures, Pakistan Journal of Biological Sciences, 2009, pp. 367-372.
Michaelsen et al., "Choice of Foods and Ingredients for Moderately Malnourished Children 6 Months to 5 Years of Age", Food and Nutrition Bulletin, vol. 30, Issue No. 3, 2009, pp. S343-S404.
U.S. Patent Office Communication for U.S. Appl. No. 17/039,492, dated Feb. 14, 2022, 20 pages.

\* cited by examiner

*Primary Examiner* — Qiuwen Mi
(74) *Attorney, Agent, or Firm* — K&L Gates LLP

(57) ABSTRACT

Use of a lentil product to increase the bioavailability of non-haem iron in a composition comprising one or more anti-nutritional factors.

16 Claims, 5 Drawing Sheets

NUTRITIONAL COMPOSITION

INCORPORATION BY REFERENCE STATEMENT

The entirety of European Application No. 18176727.8 filed Jun. 8, 2018, is hereby expressly incorporated by reference therein.

TECHNICAL FIELD OF THE INVENTION

The present invention relates to the use of a lentil product to increase the bioavailability of non-haem iron in a composition comprising anti-nutritional factors such as phytic acid e.g. a composition comprising wholegrain.

BACKGROUND OF THE INVENTION

A variety of short and long-term health benefits have been attributed to the regular intake of wholegrain e.g. a reduction in the short and long term risk of type II diabetes, obesity and, heart disease; for this reason, an increasing number of consumers are seeking out products comprising it.

In view of the health benefits and increased demand for products comprising wholegrain, more and more companies are replacing refined grain with wholegrain in their products.

Whilst the health benefits associated with wholegrain are indisputable, its presence in a product can have drawbacks. In particular, in comparison to refined grain, wholegrain ordinarily comprises more anti-nutritional factors, such as phytic acid. These anti-nutritional factors can negatively affect the absorption/bio-availability of non-haem iron from a product.

Poor absorption of non-haem iron from products, in particular cereal or legume based foods, is believed to be major factor in the etiology of iron deficiency, in particular in the infant population.

Several methods have been developed to reduce the content of anti-nutritional factors such as phytic acid in compositions comprising them e.g. pre-treatments involving fermentation, soaking, germination and/or enzymatic treatment with phytase enzyme. However, these methods have drawbacks because they may not only reduce the concentration of anti-nutritional compounds, but also other nutrients that may have health benefits. These methods also add an additional cost element to the product production.

Accordingly, there is still a need to identify alternative ways to mitigate the negative effect of anti-nutritional factors such as phytic acid on non-haem iron absorption/bioavailability, for example in compositions/products comprising wholegrain, in particular there is a need to find ways that may not suffer from one or more of the drawbacks of the prior art.

An object of the present invention is to address such a need.

Surprisingly, the inventors have now found that a lentil product may counteract the effect of one or more anti-nutritional factors such as phytic acid, on non-haem iron absorption/bioavailability. More particularly the inventors have found that adding a lentil product to a composition comprising antinutritional factors such as phytic acid e.g. a composition comprising wholegrain, may reduce the inhibitory effect of one or more anti-nutritional factor e.g. phytic acid, on the absorption/bioavailability of non-haem iron from said composition.

SUMMARY OF THE INVENTION

The invention is set out in the claims and in the detailed description included herein.

There is provided the use of a lentil product to increase the bioavailability of non-haem iron in a composition comprising one or more anti-nutritional factor.

Further provided is a composition comprising a lentil product, non-haem iron and, wholegrain, wherein the composition is a complementary nutritional composition for infants for use during the complementary feeding period.

Also provided is a method of increasing the bioavailability of non-haem iron in a composition comprising one or more anti-nutritional factor, said method comprising the step of adding to said composition a lentil product.

The lentil product may be a yellow lentil product, a red lentil product, or a combination of the foregoing.

The one or more anti-nutritional factor may be phytic acid.

The non-haem iron maybe ferrous sulfate, ferrous fumarate, ferrous bisglycinate or a combination of any of the foregoing.

The composition comprising one or more anti-nutritional factor may be a composition comprising wholegrain. The wholegrain maybe whole grain maize, wheat, rice (for example red rice), oat, corn, barley, semolina, or any combination of any of the foregoing.

Wholegrain may be comprised in the composition of the invention in a concentration of 5 to 30 w/w %.

Non haem-Iron may be comprised in the composition in a concentration of at least 1.6 mg/100 Kcal of the composition.

A composition of the invention may be used in the treatment or prevention of sub-optimal iron levels in a subject wherein said subject is an infant or child.

A composition of the invention may be used to optimize the iron status of a subject wherein said subject is an infant or child.

DETAILED DESCRIPTION

Figure 1:
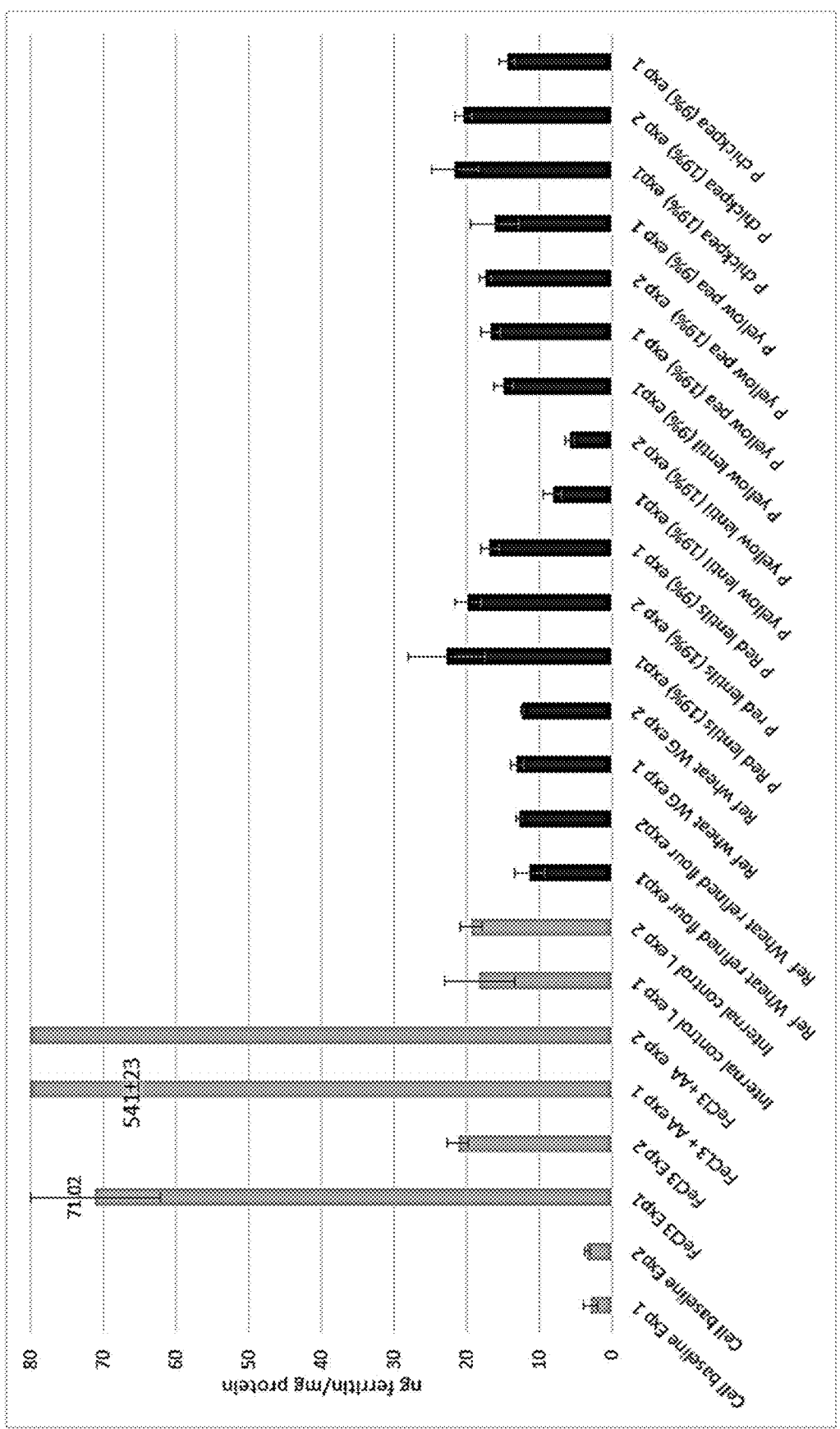
FIG. 1 Shows the iron bio-accessibility of iron intrinsically present in references and prototypes comprising different level of legumes, whole grains and milk. Results for internal controls are represented by grey bars; results for references and prototypes samples are represented by black bars.

The inventors have found that adding a lentil product to a composition comprising one or more anti-nutritional factor e.g. a composition comprising wholegrain, may increase the bioavailability of non-haem iron in said composition. Without wishing to be bound by theory the inventors believe that the lentil product may reduce/mitigate the inhibitory effect of said one or more anti-nutritional factor e.g. Phytic acid, on the absorption of non-haem iron from said composition.

In a first aspect of the invention there is provided the use of a lentil product to increase the bioavailability of non-haem iron in a composition comprising one or more anti-nutritional factor.

The term lentil product as used herein refers to a lentil or part thereof, or any composition comprising one or more lentil or one or more part of one or more lentil. The term lentil as used herein refers to a seed of a plant of the species *Lens culinaris* and subspecies *Lens Culinaris Medik.*

The lentil in the lentil product may be any type of lentil. Non-limiting examples of types of lentil include green lentils, French Green Lentils (Puy lentils), yellow lentils, red lentils, and black/beluga lentils.

The present inventors have found that red and/or yellow lentils may be particularly effective in the invention. Accordingly, in an embodiment of the invention the lentil product is selected from the group consisting of a red lentil product, a yellow lentil product and a combination of the foregoing.

In a specific embodiment the lentil product is a yellow lentil product.

The lentil product may be in any form, no limiting example of forms include dehulled whole lentils, dehulled crushed lentils, dehulled lentil flour (ground dehulled lentils), and combinations of any of the foregoing. Because crushing or grinding the lentils increases the surface area and may release actives from the lentils. Crushed or ground lentils may be more effective in the invention. Accordingly, in a more specific embodiment of the invention, the lentil product comprises crushed dehulled lentils, dehulled lentil flour, or any combination of any of the foregoing e.g. the lentil product comprises dehulled lentil flour or consists of dehulled lentil flour.

The term "anti-nutritional factor" as used herein refers to a compound that interferes with the absorption/bioavailability of non-haem iron. Non-limiting examples of anti-nutritional factors include: phytic acid, polyphenols, and calcium. Milk may also interfere with the absorption/bioavailability of non-haem iron. Accordingly, as used herein the term "anti-nutritional factor" also refers to milk.

The inventors believes that a lentil product may be particularly effective at counteracting the inhibitory effect of phytic acid on the absorption of non-haem iron from a composition. Accordingly, in an embodiment of the invention the anti-nutritional factor is phytic acid.

The term "phytic acid" as used herein refers to a myo-inositol phosphate i.e. myo-inositol monophosphate (InsP), myo-inositol bisphosphate ($InsP_2$), myo-inositol triphosphate ($InsP_3$), myo-inositol tetrakisphosphate ($InsP_4$), myo-inositol pentakisphosphate ($InsP_5$) or myo-inositol hexakisphosphate ($InsP_6$). In the context of this invention, the term "phytic acid" also includes any salt or ester of phytic acid capable of forming phytic acid in the food or beverage composition of the invention.

Anti-nutritional factors are found in a wide variety of ingredients and food products and are known to be particularly prevalent in plant derived ingredients and/or products and more particularly in wholegrains. Accordingly, the lentil product may be particularly effective when used in combination with wholegrain.

Accordingly, in an embodiment of the present invention the composition comprising an anti-nutritional factor is a composition comprising wholegrain.

The term "whole grain", as used herein refers to a grain product including the intact, ground, cracked or flaked caryopsis, whose principal anatomical components: the starchy endosperm, germ and bran, are present in the same relative proportions as they exist in the intact caryopsis. The grain product may be any grain. Non limiting examples of grain include: Amaranth *Amaranthus cruentus*, Barley *Hordeum vulgare*), Buckwheat *Fagopyrum esculentum*, Bulgur *Triticum* ssp., Corn *Zea mays* mays, Einkorn *Triticum monococcum* L, Farro/Emmer *Triticum turgidum dicoccum*, Fiono, Freekeh *Triticum turgidum* var. durum, Khorasan Grain (*triticum turgidum turanicum*), Kañiwa (*Chenopodium pallidicaule*, Millet (*Panicum miliaceum, Pennisetum Glaucum, Setaria italica, Eleusine coracana, digitaria exilis*), Oats (*Avena sativa*), Quinoa (*Chenopodium quinoa*), Rice (*Oryza sativa*), Rye (*Secale cereale*), Sorghum/Milo (*Sorghum* spp.), Spelt (*Triticum aestivum spelta*), Teff (*Eragrostis tef*), Triticale (x triticosecale rimpaui), Wheat (*Triticum aestivum; Triticum turgidum*), Wild Rice (*Zizania* spp.) semolina, and any combination of any of the foregoing.

Wholegrain maize, wheat, oat, rye, corn, semolina and rice (for example red rice) are extremely popular wholegrains employed in food products, in particular food products for infants and children.

Accordingly, in a more specific embodiment of the invention the wholegrain is selected from the group consisting of: maize, wheat, oat, rye, corn, semolina, rice and a any combination of any of the foregoing.

The term non-haem iron as used herein refers to any iron that is not attached to a haem protein. It may be Fe(III) or Fe(II). Fe(III) ions are iron ions of the +3 oxidation state. They may also be referred to as $Fe^{3+}$ ions or ferric ions. Fe(II) ions are iron ions of the +2 oxidation state. They may also be referred to as $Fe^{2+}$ ions or ferrous ions. The non-haem iron may be in the form of a salt. Non-limiting examples include: ferric citrate, ferric ammonium citrate, ferric phosphate, ferric pyrophosphate, ferric sodium diphosphate, ferrous ascorbate, ferrous carbonate, ferrous citrate, ferrous fumarate, ferrous gluconate, ferrous bisglycinate, ferrous lactate, ferrous sulfate, ferrous succinate, ferrous ammonium phosphate, ferrous L-pidolate and, any combination of any of the foregoing. The non-haem iron may also be in the form of a physiologically acceptable iron chelate such as for example NaFe EDTA (sodium iron EDTA).

Fe2+ is more bioavailable than Fe3+ and it may therefore be more beneficial if iron is added into the composition in the form of a ferrous salt or complex e.g. ferrous sulfate, ferrous fumerate, ferrous bisglycinate or a combination thereof.

In an embodiment of the present invention the non-haem iron is selected from the group consisting of ferrous sulfate, ferrous bisglycinate, ferrous fumerate and a combination of any of the foregoing.

The lentil product may be used in combination with any ingredient known to improve the absorption/bioavailability of non-haem iron from a composition. For example the lentil product may be used in combination with ascorbic acid (vitamin C) or other organic acids.

In another embodiment of the present invention there is provided the use of a lentil product and ascorbic acid to increase the bioavailability of non-haem iron in a composition comprising one or more anti-nutritional factor e.g. a composition comprising phytic acid such as a composition comprising wholegrain.

The lentil product may be used to increase the bioavailability of non-haem iron in any type of composition comprising one or more anti-nutritional factor.

The composition may for example be a nutritional product, a food product, a functional food product, a medical food, a nutritional supplement, a pharmaceutical formulation, a beverage product.

The term "food product", as used herein, refers to a product that may be safely consumed by a human or animal and includes dairy products, pet food products and, products intended for consumption by infants, young children and children. Said food product may be in solid, semi-solid or liquid form and may comprise one or more nutrients.

The term "pet food product" as used herein refers to a nutritional product that is intended for consumption by pets. A pet, or companion animal, as referenced herein, is to be understood as an animal selected from dogs, cats, birds, fish, rodents such as mice, rats, and guinea pigs, rabbits, etc.

The term "dairy products", as used herein, refers to food products produced from animals such as cows, goats, sheep, yaks, horses, camels, and other mammals. Examples of dairy products are low-fat milk (e.g. 0.1%, 0.5% or 1.5% fat), fat-free milk, milk powder, whole milk, whole milk products, butter, buttermilk, buttermilk products, skim milk, skim milk products, high milk-fat products, condensed milk, créme fraiche, cheese, ice cream and confectionery products, probiotic drinks or probiotic yoghurt type drinks.

The term "functional food product" as used herein, refers to a food product providing an additional health-promoting or disease-preventing function to the individual e.g. low GI, diabetes prevention and/or iron supplementation.

The term "medical food" as used herein refers to a special class of nutritional compositions designed to provide dietary management of certain conditions. The medical food meets certain criteria as set out by and regulated under the Orphan Drug Act of 1983 in Section 5 [360ee](b)(2)(D).

The term "nutritional supplement" as used herein, refers to a nutritional product that provides nutrients to an individual that may otherwise not be consumed in sufficient quantities by said individual.

The term "pharmaceutical formulation" as used herein, refers to a composition comprising at least one pharmaceutically active agent, chemical substance or drug.

The term "beverage product" as used herein, refers to a nutritional product in liquid or semi-liquid form that may be safely consumed by an individual.

Term "products intended for consumption by infants, young children and children" as used herein refers to products specifically formulation for consumption by infants, young children and/or children. Non-limiting examples include infant formula, follow on formula, growing up milks, baby food including infant cereals and nutritional compositions for use in the complementary feeding period e.g. infant cereals for use in the complementary feeding period.

The term "complementary feeding period" indicates the process of gradually introducing a mammal infant to what will be its adult diet and complementing the supply of its mother's milk with solid foods. For humans, the complementary feeding period typically starts at age between 4 and 6 months of infant's age and is considered completed once the infant is not anymore fed with any breast milk (or substitute infant formula), typically at 24 months. In one embodiment, the complementary feeding period is comprised between 4, for example 6, months and 24, for example 18 months of infant's age.

The term "a nutritional composition for use in the complementary feeding period" as used herein refers to a nutritional composition which is designed to be administered to an infant or young child at the time the complementary feeding period starts or afterwards. In one embodiment, the complementary nutritional composition is administered during the complementary feeding period. This nutritional composition is usually to be taken enterally, orally, parenterally or intravenously, and it usually includes a lipid or fat source, a protein source and a carbohydrate source.

In an embodiment of the invention the lentil product is used to increase the bio-availability of non-haem iron in a composition comprising one or more anti-nutritional factor wherein said composition is an infant cereal or nutritional composition for use in the complementary feeding period e.g. wherein said composition is an infant cereal for use in the complementary feeding period.

The lentil product may for example be used in conjunction with wholegrain cereal to replace part of the skimmed milk or refined cereal in an infant cereals or nutritional compositions for use in the complementary feeding period e.g infant cereals for use in the complementary feeding period, and may maintain the iron bioavailability in said product despite the increase in phytic acid due to the increase in the concentration of wholegrain cereal or other ingredients that may be a source of anti-nutritional factors in said composition.

In another aspect of the present invention there is provided a composition comprising a lentil product, non-haem iron and an anti-nutritional factor e.g. phytic acid. In an embodiment the composition comprises a lentil product, non-haem iron and wholegrain.

The composition may for example be a nutritional product, a food product, a functional food product, a medical food, a nutritional supplement, a pharmaceutical formulation, a beverage product.

The composition of the invention may comprise the lentil product in any amount for example in an effective amount. An effective amount may be any amount that increased the bioavailability of non-haem iron in a composition comprising one or more anti-nutritional factor. It is well within the purview of the skilled person to determine an effective amount. An effective amount may for example be determined by measuring the bio-availability of non-haem iron said composition before and after the addition of a lentil product and determining what concentration of lentil product results in an increase in the bio-availability of the non-haem iron in said composition. The effective amount may depend on the concentration of the anti-nutritional factors and/or the concentration of the non-haem iron in said composition.

In an embodiment of the invention the composition comprising a lentil product, non-haem iron and wholegrain is an infant cereals or nutritional compositions for use in the complementary feeding period e.g. is an infant cereal for use in the complementary feeding period.

In an embodiment the lentil product comprised in the infant cereals or nutritional compositions for use in the complementary feeding period is selected from the group consisting of a yellow lentil product, a red lentil product, and a combination of the foregoing. In a more specific embodiment the lentil product is a yellow lentil product.

The lentil product may be comprised in the infant cereal or nutritional composition for use in the complementary feeding period in any amount. It may for example be used in an effective amount.

In one embodiment, the infant cereal or complementary nutritional composition for use in the complementary feeding period comprises a lentil product in an amount of 5 to 80% w/w of the infant cereal or nutritional compositions for use in the complementary feeding period, for example in an amount in the range of at least 5 to 70% w/w, 5% to 20% w/w, 8% to 20% w/w, 9% to 20% w/w.

Non-haem Iron may be comprised in the infant cereal or nutritional composition for use in the complementary feeding period in any amount.

In one embodiment, the infant cereal or complementary nutritional composition for use in the complementary feeding period comprises non-haem iron in an amount of at least 1.6 mg of iron per 100 Kcal of the infant cereal or nutritional compositions for use in the complementary feeding period, for example in an amount in the range of at least 1.6 mg up to 3 mg of non-haem iron per 100 Kcal of the infant cereal or nutritional compositions for use in the complementary feeding period.

In a specific embodiment the non-haem iron is selected from the group consisting of: ferrous sulfate, ferrous bisglycinate, ferrous fumerate and any combination of any of the foregoing.

Whole grain may be comprised in the infant cereal or nutritional compositions for use in the complementary feeding period in any amount. It may for instance constitute 100% of the cereal flour comprised in the infant cereal or nutritional compositions for use in the complementary feeding period.

In one embodiment, the infant cereal or nutritional compositions for use in the complementary feeding period comprises an amount of wholegrain cereal flour ranging from 10 to 90% w/w, for example 15 to 70% w/w.

In a specific embodiment the infant cereal or nutritional composition for use in the complementary feeding period comprise wholegrain cereal flour in an amount ranging from 10% to 55% w/w of cereal flour comprised in the composition, for example, the composition comprises 45% to 90% w/w of refined flour and 10 to 55% w/w of whole grain flour.

In another specific embodiment the infant cereal or nutritional composition for use in the complementary feeding period, and comprises whole grain an amount ranging from 40 to 85% w/w or 50 to 90% w/w of cereal flour for example it comprises 40 to 70% w/w of refined flour and 30% to 60% w/w of whole grain flour.

In another specific embodiment the infant cereal or nutritional composition for use in the complementary feeding period comprises whole grain in an amount ranging from 40 to 85% w/w or 50 to 90% w/w of cereal flour for example it comprises 40 to 70% w/w of refined flour and 30% to 60% w/w of whole grain flour.

In an embodiment the infant cereal or nutritional composition for use in the complementary feeding period comprises 5 to 30% w/w of whole grain, at least 1.6 mg per 100 kcal of non haem iron and 5 to 20% w/w of a lentil product, for example 5 to 20% w/w or 5 to 16% w/w wholegrain, at least 1.6 mg per 100 kcal of non haem iron and 5 to 20% w/w of a lentil product.

In an embodiment the whole grain is selected from the group consisting of wholegrain maize, wheat, rice, oat, corn, barley, rye, semolina, and any combination of any of the foregoing.

The infant cereal or nutritional composition for use in the complementary feeding period according to the invention may also comprise any ingredient ordinarily found in this type of composition.

The infant cereal or nutritional compositions for use in the complementary feeding period may for example further comprises at least one carbohydrate-based ingredient with a low glycemic index.

In an embodiment, the infant cereal or nutritional compositions for use in the complementary feeding period comprises at least one carbohydrate-based ingredient selected from the group consisting of: Resistant starches, Amylose, Sucrose, Lactose, Isomaltulose, Maltitol, Galactose, Fructose, Isomalt, Xilitol and Polydextrose.

In an embodiment, the infant cereal or nutritional compositions for use in the complementary feeding period comprises a sugar or mixtures thereof. In a specific embodiment, the total amount of sugars ranges from 0 to 30% w/w, for example from 0 to 20% w/w, for example between 2 to 25% w/w, 5 to 25% w/w, 5 to 18% w/w.

In another embodiment, the amount of added sugars in the infant cereal or nutritional compositions for use in the complementary feeding period ranges from 0 to 30% w/w, for example from 1 to 20% w/w or from 5 to 15% w/w.

In one embodiment, the infant cereal or nutritional compositions for use in the complementary feeding period comprises an amount of added sugars with low glycemic index which ranges from 0 to 30% w/w, for example from 1 to 20% w/w or from 5 to 15% w/w. The low glycemic index sugar may for example be selected in the group consisting of: lactose, galactose, fructose, isomaltulose and a combination of any of the foregoing.

In an embodiment, the infant cereal or nutritional compositions for use in the complementary feeding period comprises an edible fat or mixtures thereof, for example it comprises vegetable oils (for example rapeseed oil, palm oil, corn oil, soy oil, coconut oil and/or sunflower oil) and/or fats derived from milk.

In a specific embodiment, the infant cereal or nutritional compositions for use in the complementary feeding period comprises fats in an amount ranging from 8 to 20% w/w of the composition, for example ranging from 10 to 20% w/w, for example ranging from 10 to 17% w/w or from 10 to 15% w/w. The energy provided by fats may range from 22 to 40%, for example between 27 and 38% of the total energy intake provided by the infant cereal or nutritional compositions for use in the complementary feeding period.

In another embodiment, the infant cereal or nutritional compositions for use in the complementary feeding period doesn't comprise fats.

In an embodiment, the infant cereal or nutritional compositions for use in the complementary feeding period comprises total dietary fiber in a total amount ranging from 0 to 25% w/w, 0 to 20% w/w for example from 2 to 22% w/w; for example from 2 to 12% w/w, for example 0 to 10% w/w, for example from 6 to 10% w/w, 1 to 8% w/w, 5 to 18% w/w or from 1.5 to 7% w/w.

In an embodiment, the infant cereal or nutritional compositions for use in the complementary feeding period comprises a milk-based ingredient or mixtures thereof. In a specific embodiment, the infant cereal or nutritional compositions for use in the complementary feeding period comprises a milk-based ingredient in an amount ranging from 0 to 35% w/w, for example 0 to 30% w/w, for example from 1 to 25% w/w, for example from 5 to 25% w/w.

In a more specific embodiment, the complementary nutritional composition comprises milk-based ingredients having a GI lower or equal to 30. The milk based ingredient may be bovine milk or goats milk e.g. it may be bovine skimmed milk.

In an embodiment, the infant cereal or nutritional compositions for use in the complementary feeding period comprises one or more legumes in addition to the lentil product.

In a specific embodiment, the infant cereal or nutritional compositions for use in the complementary feeding period comprises one or more legumes, in addition to the lentil product, in an amount ranging from 5 to 40% w/w, for example from 8 to 30% w/w, for example from 10 to 25% w/w. In a more specific embodiment each of the one or more legumes or the combination of said legumes has a GI lower or equal to 65, for example 50.

In one embodiment, the infant cereal or nutritional compositions for use in the complementary feeding period comprises a fruit or mixtures thereof. In a specific embodiment, the infant cereal or nutritional compositions for use in the complementary feeding period comprises fruits in an amount ranging from 0 to 25% w/w, for example from 1 to 18% w/w, 1 to 20% w/w, 1 to 15% w/w.

In a specific embodiment, the present invention provides an infant cereal or nutritional compositions for use in the complementary feeding period comprising:
- cereal flour in amount ranging from 20 to 90% w/w wherein 5 to 100% of the cereal flour is wholegrain flour;
- sugar in amount ranging from 0 to 30% w/w, for example from 0 to 20% w/w, for example between 5 to 18% w/w;
- added sugar with low glycemic index in amount ranging from 0 to 30% w/w, for example from 1 to 20% w/w, for example from 5 to 15% w/w;
- fat in an amount ranging from 8 to 20% w/w of the composition, for example ranging from 10 to 17% w/w, for example from 10 to 15% w/w;
- total amount of dietary fiber in amount ranging from 0 to 25% w/w, for example from 2 to 25% w/w;
- added fiber in amount ranging from 0 to 20% w/w;
- milk-based ingredient in an amount ranging from 0 to 30% w/w, for example from 1 to 25% w/w, for example from 5 to 25% w/w;
- legume (in addition to a lentil product) in amount ranging from 0 to 40% w/w, for example from 5 to 40% w/w;
- fruit in an amount ranging from 0 to 25% w/w, for example from 1 to 18% w/w.
- Lentil flour (red or yellow or a combination thereof) in an amount ranging from 2 to 70% w/w e.g. 5 to 15% w/w.
- Non haem-iron in an amount equating to at least 1.6 mg per 100 Kcal of the composition.

In another specific embodiment, the present invention provides an infant cereal or nutritional compositions for use in the complementary feeding period comprising:
- cereal flour in amount ranging from 20 to 70% w/w, for example 30 to 55% w/w of cereal flours;
- sugar in amount ranging from 0 to 30% w/w, for example from 0 to 20% w/w, for example between 5 to 18% w/w;
- added sugar with low glycemic index in amount ranging from 0 to 30% w/w, for example from 1 to 20% w/w, for example from 5 to 15% w/w;
- fat in an amount ranging from 8 to 20% w/w of the composition, for example ranging from 10 to 17% w/w, for example from 10 to 15% w/w;
- total amount of dietary fiber in amount ranging from 2 to 12% w/w, for example from 6 to 10% w/w;
- added fiber in amount ranging from 0 to 10% w/w, for example from 1 to 8% w/w, for example from 1.5 to 7% w/w;
- milk-based ingredient in an amount ranging from 0 to 35% w/w, for example 0 to 30% w/w, for example from 1 to 25% w/w, for example from 5 to 25% w/w;
- legume (in addition to a lentil product) in amount ranging from 5 to 40% w/w, for example from 8 to 30% w/w, for example from 10 to 25% w/w;
- fruit in an amount ranging from 0 to 25% w/w, for example from 1 to 18% w/w.
- Lentil flour (red or yellow or a combination thereof) in an amount ranging from 2 to 70% w/w e.g. 5 to 15% w/w.
- Non haem-iron in an amount equating to at least 1.6 mg per 100 Kcal of the composition.

In yet another specific embodiment, the present invention provides an infant cereal or nutritional compositions for use in the complementary feeding period comprising:
- cereal flour in amount ranging from 20 to 70% w/w, for example 30 to 55% w/w of cereal flours, for example 33 to 50% w/w;
- sugar in amount ranging from 0 to 30% w/w, for example from 0 to 25% w/w, for example from 5 to 25% w/w, for example from 0 to 20% w/w, for example between 5 to 18% w/w;
- added sugar with low glycemic index in amount ranging from 0 to 30% w/w, for example from 1 to 20% w/w, for example from 5 to 15% w/w;
- fat in an amount ranging from 8 to 20% w/w of the composition, for example ranging from 10 to 17% w/w, for example from 10 to 15% w/w;
- total amount of dietary fiber in amount ranging from 2 to 12% w/w, for example from 6 to 10% w/w;
- added fiber in amount ranging from 0 to 10% w/w, for example from 1 to 8% w/w, for example from 1.5 to 7% w/w;
- milk-based ingredient in an amount ranging from 0 to 35% w/w, for example from 0 to 30% w/w, for example from 1 to 25% w/w, for example from 5 to 25% w/w;
- legume (in addition to the lentil product) in amount ranging from 5 to 40% w/w, for example from 5 to 40% w/w, for example from 8 to 30% w/w, for example from 10 to 25% w/w;
- fruit in an amount ranging from 0 to 25% w/w, for example from 1 to 18% w/w.
- Lentil flour (red or yellow or a combination thereof) in an amount ranging from 2 to 70% w/w e.g. 5 to 15% w/w.
- Non haem-iron in an amount equating to at least 1.6 mg per 100 Kcal of the composition.

In another specific embodiment, the present invention provides an infant cereal or nutritional compositions for use in the complementary feeding period comprising:
- cereal flour in amount ranging from 33 to 50% w/w;
- sugar in amount ranging from from 5 to 25% w/w;
- added sugar with low glycemic index in amount ranging from 5 to 15% w/w;
- fat in an amount ranging from 10 to 17% w/w;
- total amount of dietary fiber in amount ranging 6 to 10% w/w;

added fiber in amount ranging from 0 to 10% w/w, for example from 1 to 8% w/w, for example from 1.5 to 7% w/w;
milk-based ingredient in an amount ranging from 5 to 25% w/w;
legume (in addition to the lentil product) in amount ranging from 5 to 40% w/w, for example from 5 to 40% w/w, for example from 8 to 30% w/w, for example from 10 to 25% w/w;
fruit in an amount ranging from 0 to 25% w/w, for example from 1 to 18% w/w.
Lentil flour (red or yellow or a combination thereof) in an amount ranging from 2 to 70% w/w e.g. 5 to 15% w/w.
Non haem-iron in an amount equating to at least 1.6 mg per 100 Kcal of the composition.

In a further specific embodiment, the present invention provides an infant cereal or nutritional compositions for use in the complementary feeding period comprising:
cereal flour in amount ranging from 33 to 50% w/w;
sugar in amount ranging from 5 to 25% w/w;
added sugar with low glycemic index in amount ranging from 5 to 15% w/w;
fat in an amount ranging from 10 to 17% w/w;
total amount of dietary fiber in amount ranging from 6 to 10% w/w;
added fiber in amount ranging from 1.5 to 7% w/w;
milk-based ingredient in an amount ranging from 5 to 25% w/w;
legume (in addition to a lentil product) in amount ranging from 10 to 25% w/w;
fruit in an amount ranging from 1 to 18% w/w;
wherein the complementary nutritional composition comprises 0 to 30% w/w of cereal refined flour and 0 to 55% of cereal whole grain flours.
Lentil flour (red or yellow or a combination thereof) in an amount ranging from 2 to 70% w/w e.g. 5 to 15% w/w.
Non haem-iron in an amount equating to at least 1.6 mg per 100 Kcal of the composition.

In yet a further specific embodiment, the present invention provides an infant cereal or nutritional compositions for use in the complementary feeding period comprising:
cereal flour in amount ranging from 33 to 50% w/w;
sugar in amount ranging from 5 to 25% w/w;
added sugar with low glycemic index in amount ranging from 5 to 15% w/w;
fat in an amount ranging from 10 to 17% w/w;
total amount of dietary fiber in amount ranging from 6 to 10% w/w;
added fiber in amount ranging from 0 to 10% w/w, for example from 1 to 8% w/w, for example from 1.5 to 7% w/w;
milk-based ingredient in an amount ranging from 5 to 25% w/w;
legume (in addition to a lentil product) in amount ranging from 10 to 25% w/w;
fruit in an amount ranging from 1 to 18% w/w;
Lentil flour (red or yellow or a combination thereof) in an amount ranging from 2 to 70% w/w e.g. 5 to 15% w/w.
Non haem-iron in an amount equating to at least 1.6 mg per 100 Kcal of the composition.
wherein the complementary nutritional composition comprises 0 to 30% w/w of cereal refined flour and 0 to 55% w/w of cereal whole grain flours.

In a further specific embodiment, the present invention provides an infant cereal or nutritional compositions for use in the complementary feeding period comprising:
cereal flour in amount ranging from 33 to 50% w/w;
sugar in amount ranging from 5 to 25% w/w;
added sugar with low glycemic index in amount ranging from 5 to 15% w/w;
fat in an amount ranging from 10 to 17% w/w;
total amount of dietary fiber in amount ranging from 6 to 10% w/w;
added fiber in amount ranging from 1.5 to 7% w/w;
milk-based ingredient in an amount ranging from 5 to 25% w/w;
legume (in addition to the lentil product) in amount ranging from 10 to 25% w/w;
fruit in an amount ranging from 0 to 25% w/w, for example from 1 to 18% w/w,
Lentil flour (red or yellow or a combination thereof) in an amount ranging from 2 to 70% w/w e.g. 5 to 15% w/w.
Non haem-iron in an amount equating to at least 1.6 mg per 100 Kcal of the composition.
Wherein the complementary nutritional composition comprises 0 to 30% w/w of cereal refined flour and 0 to 55% w/w of cereal whole grain flours.

In a further specific embodiment, the present invention provides an infant cereal or nutritional compositions for use in the complementary feeding period comprising:
cereal flour in amount ranging from 33 to 50% w/w;
sugar in amount ranging from 5 to 25% w/w;
added sugar with low glycemic index in amount ranging from 5 to 15% w/w;
fat in an amount ranging from 10 to 17% w/w;
total amount of dietary fiber in amount ranging from 6 to 10% w/w;
added fiber in amount ranging from 1.5 to 7% w/w;
milk-based ingredient in an amount ranging from 5 to 25% w/w;
legume (in addition to a lentil product) in amount ranging from 5 to 40% w/w, for example from 5 to 40% w/w, for example from 8 to 30% w/w, for example from 10 to 25% w/w;
fruit in an amount ranging from 1 to 18% w/w;
wherein the complementary nutritional composition comprises 0 to 30% w/w of cereal refined flour and 0 to 55% w/w of cereal whole grain flours.
Lentil flour (red or yellow or a combination thereof) in an amount ranging from 2 to 70% w/w e.g. 5 to 15% w/w.
Non haem-iron in an amount equating to at least 1.6 mg per 100 Kcal of the composition.

In another embodiment, the present invention provides an infant cereal or nutritional compositions for use in the complementary feeding period comprising:
cereal flour in amount ranging from 20 to 90% w/w, for example 40 to 85% w/w of cereal flours;
total sugar in amount ranging from 0 to 30% w/w, for example from 0 to 20% w/w, for example between 5 to 18% w/w;
added sugar with low glycemic index in amount ranging from 0 to 30% w/w, for example from 1 to 20% w/w, for example from 5 to 15% w/w;
fat in an amount ranging from 0 to 10% w/w of the composition, for example ranging from 0 to 8% w/w, for example from 0 to 5% w/w;
total amount of dietary fiber in amount ranging from 0 to 25% w/w, for example from 2 to 22% w/w;
added fiber in amount ranging from 0 to 20% w/w, for example from 5 to 18% w/w;

legume (in addition to a lentil product) in amount ranging from 5 to 40% w/w, for example from 8 to 30% w/w, for example from 10 to 25% w/w;

fruit in an amount ranging from 0 to 25% w/w, for example from 1 to 18% w/w.

Lentil flour (red or yellow or a combination thereof) in an amount ranging from 2 to 70% w/w e.g. 5 to 15% w/w.

Non haem-iron in an amount equating to at least 1.6 mg per 100 Kcal of the composition.

In another embodiment, the present invention provides an infant cereal or nutritional compositions for use in the complementary feeding period comprising:

cereal flour in amount ranging from 20 to 90% w/w, for example 40 to 85% w/w, for example for example 50 to 90% w/w of cereal flours;

total sugar in amount ranging from 0 to 30% w/w, for example from 5 to 25% w/w, for example from 0 to 20% w/w, for example from 2 to 20% w/w, for example between 5 to 18% w/w;

added sugar with low glycemic index in amount ranging from 0 to 30% w/w, for example from 1 to 20% w/w, for example from 5 to 15% w/w;

fat in an amount ranging from 0 to 10% w/w of the composition, for example ranging from 0 to 5% w/w;

total amount of dietary fiber in amount ranging from 0 to 25% w/w, for example from 2 to 22% w/w;

added fiber in amount ranging from 0 to 20% w/w, for example from 5 to 18% w/w;

legume (in addition to a lentil product) in amount ranging from 5 to 40% w/w, for example from 8 to 30% w/w, for example from 10 to 25% w/w;

fruit in an amount ranging from 0 to 25% w/w, for example from 1 to 18% w/w.

Lentil flour (red or yellow or a combination thereof) in an amount ranging from 2 to 70% w/w e.g. 5 to 15% w/w.

Non haem-iron in an amount equating to at least 1.6 mg per 100 Kcal of the composition.

In a further embodiment, the present invention provides an infant cereal or nutritional compositions for use in the complementary feeding period comprising:

cereal flour in amount ranging from 50 to 90% w/w;

total sugar in amount ranging from 5 to 18% w/w;

added sugar with low glycemic index in amount ranging from 5 to 15% w/w;

fat in an amount ranging from 0 to 10% w/w of the composition, for example ranging from 0 to 5% w/w;

total amount of dietary fiber in amount ranging from 2 to 22% w/w;

added fiber in amount ranging from 0 to 20% w/w, for example from 5 to 18% w/w;

legume (in addition to a lentil product) in amount ranging from 5 to 40% w/w, for example from 8 to 30% w/w, for example from 10 to 25% w/w;

fruit in an amount ranging from 0 to 25% w/w, for example from 1 to 18% w/w. wherein the complementary nutritional composition comprises 30 to 50% w/w of cereal refined flour and 20 to 40% of cereal whole grain flours.

Lentil flour (red or yellow or a combination thereof) in an amount ranging from 2 to 70% w/w e.g. 5 to 15% w/w.

Non haem-iron in an amount equating to at least 1.6 mg per 100 Kcal of the composition.

In a further embodiment, the present invention provides an infant cereal or nutritional compositions for use in the complementary feeding period comprising:

cereal flour in amount ranging from 50 to 90% w/w;

total sugar in amount ranging from 5 to 18% w/w;

added sugar with low glycemic index in amount ranging from 5 to 15% w/w;

fat in an amount ranging from 0 to 10% w/w of the composition, for example ranging from 0 to 5% w/w;

total amount of dietary fiber in amount ranging from 2 to 22% w/w;

added fiber in amount ranging from 5 to 18% w/w;

legume (in addition to a lentil product) in amount ranging from 10 to 25% w/w;

fruit in an amount ranging from 1 to 18% w/w;

wherein the complementary nutritional composition comprises 30 to 50% w/w of cereal refined flour and 20 to 40% of cereal whole grain flours.

Lentil flour (red or yellow or a combination thereof) in an amount ranging from 2 to 70% w/w e.g. 5 to 15% w/w.

Non haem-iron in an amount equating to at least 1.6 mg per 100 Kcal of the composition.

In a further embodiment, the present invention provides an infant cereal or nutritional compositions for use in the complementary feeding period comprising:

cereal flour in amount ranging from 20 to 70% w/w, for example 30 to 55% w/w of cereal flours, for example 33 to 50% w/w;

sugar in amount ranging from 0 to 30% w/w, for example from 0 to 25% w/w, for example from 5 to 25% w/w, for example from 0 to 20% w/w, for example between 5 to 18% w/w;

added sugar with low glycemic index in amount ranging from 0 to 30% w/w, for example from 1 to 20% w/w, for example from 5 to 15% w/w;

fat in an amount ranging from 8 to 20% w/w of the composition, for example ranging from 10 to 17% w/w, for example from 10 to 15% w/w;

total amount of dietary fiber in amount ranging from 2 to 12% w/w, for example from 6 to 10% w/w;

added fiber in amount ranging from 0 to 10% w/w, for example from 1 to 8% w/w, for example from 1.5 to 7% w/w;

milk-based ingredient in an amount ranging from 0 to 35% w/w, for example from 0 to 30% w/w, for example from 1 to 25% w/w, for example from 5 to 25% w/w;

legume (in addition to a lentil product) in amount ranging from 5 to 40% w/w, for example from 5 to 40% w/w, for example from 8 to 30% w/w, for example from 10 to 25% w/w;

fruit in an amount ranging from 0 to 25% w/w, for example from 1 to 18% w/w;

Lentil flour (red or yellow or a combination thereof) in an amount ranging from 2 to 70% w/w e.g. 5 to 15% w/w.

Non haem-iron in an amount equating to at least 1.6 mg per 100 Kcal of the composition.

OR cereal flour in amount ranging from 20 to 90% w/w, for example 40 to 85% w/w, for example for example 50 to 90% w/w of cereal flours;

total sugar in amount ranging from 0 to 30% w/w, for example from 5 to 25% w/w, for example from 0 to 20% w/w, for example from 2 to 20% w/w, for example between 5 to 18% w/w;

added sugar with low glycemic index in amount ranging from 0 to 30% w/w, for example from 1 to 20% w/w, for example from 5 to 15% w/w;

fat in an amount ranging from 0 to 10% w/w of the composition, for example ranging from 0 to 8% w/w, for example from 0 to 5% w/w;

total amount of dietary fiber in amount ranging from 0 to 25% w/w, for example from 2 to 22% w/w;

added fiber in amount ranging from 0 to 20% w/w, for example from 5 to 18% w/w;

legume (in addition to a lentil product) in amount ranging from 5 to 40% w/w, for example from 8 to 30% w/w, for example from 10 to 25% w/w;

fruit in an amount ranging from 0 to 25% w/w, for example from 1 to 18% w/w;

Lentil flour (red or yellow or a combination thereof) in an amount ranging from 2 to 70% w/w e.g. 5 to 15% w/w.

Non haem-iron in an amount equating to at least 1.6 mg per 100 Kcal of the composition.

When the complementary nutritional composition is an infant cereal product, it may comprise at least 0.48 g/100 kJ of a protein source, at most 1.1 g/100 kJ of a lipid source and a carbohydrate source.

Infant cereals are known in the art. Infant cereals are compositions containing cereals to be administered to infants. They are usually to be administered using a spoon, and may be offered as dry cereal for infants, for example. Also ready to serve infant cereals are within the scope of the present invention. The codex alimentarius offers guidance on what ingredients an infant cereal should contain. Infant cereals may be intended to be reconstituted either in water or in milk.

Typically, the caloric density as well as the amounts and kinds of proteins, carbohydrates and lipids present in the infant cereal should be carefully adjusted to the needs of the infant and are dependent on the infant stage of development and age.

It is well known that the requirements for nutrition of an infant changes with the development and age of the infant, and the composition of the infant cereal ideally reflects this change.

Hence, a standard infant cereal (to be prepared with milk) according to the present invention to be to be administered to infants at the age of 4-6 months may have an energy density of 220-240 kJ/15 g, 0.8-1.2 g/15 g of a protein source, 0.1-0.3 g of a fat source and 12.3-12.7 g/15 g of a carbohydrate source. Such an infant cereal may contain, for example, Rice flour, Maize Maltodextrin, Vitamin C, lentil flour and non-haem iron.

A standard infant cereal (to be prepared with milk) according to the present invention to be to be administered to infants at the age of 6-12 months may have an energy density of 220-240 kJ/15 g, 1.5-1.9 g/15 g of a protein source, 0.2-0.4 g of a fat source and 11.1-11.5 g/15 g of a carbohydrate source. Such an infant cereal may contain, for example, Wheat flour, Semolina from wheat, non-haem Iron, lentil flour, Vitamin C, Niacin, Vitamin B6, Thiamin, and Maize Maltodextrin.

Hence, an infant cereal to be prepared with water according to the present invention to be administered to infants from the age of 4-6 months may have per 100 g, energy density of 400-420 kcal 100 g, 10-16 g of a protein source, 7-17 g of a fat source and 50-75 g of a carbohydrate source. Such an infant cereal may contain, for example, Rice flour, Maize Maltodextrin, Vitamin C, lentil flour, and non-haem iron.

An infant cereal according to the present invention may for example be to be administered to infants at the age of 6-12 months. Such an infant cereal may contain, for example, Wheat flour, Semolina from wheat, non-haem Iron, lentil flour, Vitamin C, Niacin, Vitamin B6, Thiamin, and Maize Maltodextrin, non-haem iron.

Infant cereals may be prepared from one or more milled cereals, which may constitute at least 25 weight-% of the final mixture on a dry weight basis.

The infant cereals of the present invention are preferably prepared from a single grain—like rice cereal or wheat cereal—because single grain compositions are less likely to cause an allergic reactions.

Typically, infants cereals are to be mixed with water or milk before consumption. For example 15 g of an infant cereal of the present invention may be to be mixed with 45 mL (complete infant cereal) of water or 90 ml of milk (standard infant cereal) respectively.

The expression "carbohydrate-based ingredient" or "carbohydrate-based ingredients" in the context of the present invention indicates a food ingredient consisting of or comprising one or more carbohydrates. Non-limiting examples of carbohydrate based ingredients are: cereal flours (for example whole grain or refined flour from maize, wheat, rice, oat), cereal starches (for example from maize, wheat, oath, rice) sugars [honey, monosaccharides (eg. Galactose, fructose, glucose), disaccharides (eg. Sucrose, lactose, isomaltulose, maltose)], oligosaccharides (fructo-oligosaccharides, galacto-oligosaccharides, gluco-oligosaccharides, maltodextrines), polysaccharides (eg. resistant starches), fibers (soluble and insoluble), pulses [for example Green lentils, red lentils, yellow lentils, mung bean, cow peas, chick peas, butter bean, black eye bean, kidney bean, pea, pigeon pea, soya bean, haricot & navy beans, blacked bean, Soybean, Pea, Lupin, Faba bean, Mung Beans, Chickpeas, Cowpea, Carob, Beans white/green/black/red, Navy beans, Lima beans, Pinto beans, Pigeon Pea, Black gram, Carioguinha beans, Bambara bean (*Vigna* subterranean), Yam bean, Canola flour, Flaxseed Powder, Chestnut flour], fruit, milk-based ingredients (for example powder skimmed or whole milk).

The expressions "sugar" or "sugars" within the context of the present invention comprises available monosaccharides (eg. Galactose, fructose, glucose) available disaccharides (eg. Sucrose, lactose, isomaltulose, maltose) or mixtures thereof.

Within the context of the present invention the term "added sugar" indicates an ingredient mainly or totally constituted by sugar which is added to the composition and whose content in sugar contributes to the total sugar content of the composition.

The total sugar content of the composition is provided by the sum of amount of sugar naturally present in ingredients used in the recipe (for example from cereal flour), those possibly produced during processing plus the amount of added sugar. As it will be apparent to the person skilled in the art, the total amount of sugars will also comprise any sugar amount which may be released by ingredients used in the recipe during processing due to the specific conditions used (for example comprising partial hydrolysis of starch). Determination of total sugars in the composition according to the invention may be carried out according to methods well known to the person skilled in the art.

For example, for quantification of total sugars in Infant cereals products the following method can be used:

The quantification of mono- and disaccharides in infant cereal samples can be completed by weighing a 1-3±0.001 gram sample into a 100 mL volumetric flask and 60 milliliters of demineralized water were added. Mono- and disaccharides contained in the samples are extracted by placing the flasks into a 70° C. water bath for 20 min with constant agitation. Samples are cooled to room temperature and more demineralized water is added to make up the mark on each volumetric flask, stoppers placed and closed flasks were shaken vigorously. Samples are then filtered through folded filter paper (N° 597, 150 mm Ø) and through a 0.2 µm HPLC-filter before injection (25 mm Ø, 8825-P-2 Infochroma AG). A solution containing monomeric glucose, dimeric lactose, sucrose, maltose, isomaltulose, and maltooligosaccharides having a degree of polymerization ranging from 3-7 is prepared as standard for peak identification and saccharide quantification.

Filtered samples are injected into chromatograph after degassing the eluents (demineralized water, 18 MΩ·cm minimum; 300 mM NaOH; 500 mM NaOH with 150 mM NaOAc) by sparging helium for 20-30 min and allowing the system to equilibrate. The following chromatographic conditions may be used: CarboPac PA1 (Dionex) column and guard column; 20 µL injection volume; 300 mM NaOH eluent with 0.6 mL/min flow rate as post column addition; 22° C. temperature.

The expression "milk-based ingredient" or "milk-based ingredients" in the context of the present invention identifies carbohydrate containing ingredients derived from mammal milk for example cow, goat and/or buffalo or mixtures thereof. Non-limiting examples of such ingredients comprise: fresh milk, concentrated milk, powder milk, whole milk, skimmed and/or semi-skimmed milk.

As it will be apparent to the skilled person, milk-based ingredients according to the present invention may bring additional nutrients beyond carbohydrates to the composition, such as for example proteins and fats.

Within the context of the present invention the term "added sugar with low glycemic index" indicates added sugar as above defined which is caractherized by having a low glycaemic index. For the sake of clarity, the amount of lactose contained in any milk-based ingredient used in the recipe, will also account as added sugar with low glycaemic index.

The expressions "fiber" or "fibers" or "dietary fiber" or "dietary fibers" within the context of the present invention indicates the indigestible portion, in the small intestine, of food derived from plants which comprises two main components: soluble fiber, which dissolves in water and insoluble fiber. Mixtures of fibers are comprised within the scope of the terms above mentioned. Soluble fiber is readily fermented in the colon into gases and physiologically active byproducts, and can be prebiotic and viscous. Insoluble fiber does not dissolve in water, is metabolically inert and provides bulking, or it can be prebiotic and metabolically ferment in the large intestine. Chemically, dietary fiber consists of non-starch polysaccharides such as arabinoxylans, cellulose, and many other plant components such as resistant starch, resistant dextrins, inulin, lignin, chitins, pectins, beta-glucans, and oligosaccharides. Non-limiting examples of dietary fibers are: prebiotic fibers such as Fructo-oligosaccharides (FOS), inulin, galacto-oligosaccharides (GOS), fruit fiber, vegetable fiber, cereal fiber, resistant starch such as high amylose corn starch. As fibers are not digestible, they do not contain available carbohydrates and on this basis they do not contribute to the GI or GL of the composition they're part of.

Within the context of the present invention the term "added fiber" or "added dietary fiber" indicates an ingredient mainly or totally constituted by fiber which is added to the composition and whose content in fiber contributes to the total fiber content of the composition. The total fiber content of the composition is provided by the sum of amount of fiber naturally present in ingredients used in the recipe (for example from whole grain cereal flour) plus amount of added fiber.

Within the context of the present invention, the term "fruit" or "fruits" indicates ingredients derived from fruit such as for example fresh fruit, fruit paste, dried fruit, fruit extracts and/or centrifugates. Mixtures of such ingredients are also comprised within the scope of the terms above mentioned. Non-limiting examples of fruit according to the present invention are: apple, apricot, banana, cherry, pear, strawberry, Mango, Orange, peach.

The expression "fat" or "fat source" or "lipid" or "lipid source" or "fats" in the context of the present invention indicates an edible solid or liquid fat or mixtures thereof. Not limiting categories of fats are those from animal, fish or vegetable origins. Non limiting examples of fats which could be used according to the present invention are: fish oil, cocoa butter, cocoa butter equivalents (CBE), cocoa butter substitutes (CBS), vegetable oils (for example rapeseed oil, palm oil, corn oil, soy oil, coconut oil and/or sunflower oil) and butter oils amongst others.

In the context of the present invention, where amounts of certain ingredients (such as, for example, sugars, fats, dietary fibers etc), are indicated which may result from different constituents incorporated in the recipe then such amounts will reflect the total content of that ingredient in the composition, irrespective of the component it is derived from.

On the other hand, when in the present invention reference is made to an "added" ingredient (such as for example added fibers, added sugars with low glycemic index etc), then only the amount of the component mainly or totally constituted by that ingredient should be accounted in the calculation.

The composition as disclosed herein may be used to optimize or maintain the iron status/iron levels in a subject or may be used in the treatment and/or prevention of iron deficiency in a subject.

The term subject as used herein refers to a human or animal e.g. a human infant or young child or child.

The term "infant" as used herein refers to a human under the age of about 12 months e.g. up to 12 months of age.

The term "young child" as used herein refers to a child older than about 12 months and up until about 5 years of age (including toddlers) for example a child older than 12 months of age until 5 years of age.

The term "child" as used herein refers to a human up to the age of about eighteen for example up to the age of 18.

In another aspect of the present invention there is provided a composition as disclosed herein for use to maintain or optimise the iron status of a subject.

In another aspect of the present invention there is provided a composition as disclosed herein for use in the treatment or prevention of iron deficiency in a subject.

The term "prevention" as used herein refers to the prevention of a condition or disorder completely, or partially (i.e., a milder form occurs and/or occurs later). The terms prevention also comprises a reduction in the risk of the condition or disorder occurring or in the severity of the condition or disorder, it also encompasses a reduction in the frequency of the occurrence of conditions or disorders.

A reduction in the risk of a condition or disorder means that the condition or disorder is less likely to occur compared to an appropriate and usual reference (such as the general population or normal weight infants or young children) e.g. in comparison to infants young children or children not being fed a composition of the invention.

In the context of the present invention, mentioned percentages are weight/weight percentages unless otherwise stated.

Nutritional compositions for use in the complementary feeding period e.g. infant cereals for use in the complementary feeding period may be sold in a dry format for reconstitution e.g. with milk or water. In the context of the present invention all weights and concentration values are given with reference to the dry weight of such a product.

The term "and/or" used in the context of the "X and/or Y" should be interpreted as "X", or "Y", or "X and Y".

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 1 to 8, from 3 to 7, from 4 to 9, from 3.6 to 4.6, from 3.5 to 9.9, and so forth.

All references to singular characteristics or limitations of the present invention shall include the corresponding plural characteristic or limitation, and vice versa, unless otherwise specified or clearly implied to the contrary by the context in which the reference is made.

Unless defined otherwise, all technical and scientific terms used herein have the same meaning as commonly understood by one of ordinary skill in the art.

It should be noted that embodiments and features described in the context of one of the aspects of the present invention also apply to the other aspects and embodiments of the invention mutatis mutandis.

The compositions for use according to the invention are herein described by different parameters, such as the ingredients, nutritional composition formats, uses, target groups etc. It should be noted that embodiments, features and exemplary embodiments described in the context of one of the parameters of the composition for use according to the invention, may also be combined with other embodiments, features and exemplary embodiments described in the context of another parameter, unless expressly stated otherwise.

Any reference to prior art documents in this specification is not to be considered an admission that such prior art is widely known or forms part of the common general knowledge in the field. As used in this specification, the words "comprises", "comprising", and similar words, are not to be interpreted in an exclusive or exhaustive sense. In other words, they are intended to mean "including, but not limited to".

The invention will now be described in further details in the following non-limiting examples.

EXAMPLES

Example 1

Material and Methods:

Iron bioaccessibility from processed cereals was evaluated using the Caco-2 cells coupled with in vitro digestions model as described by Glahn et al. (Glahn et al, 1998). In brief, first the food matrix undergoes a simulated gastric digestion with pepsin at pH=2, 37° C. for 1 hour. This step is followed by a simulated intestinal digestion with pancreatin and bile at pH=7, 37° C. for 2 hours. This second step takes place on a dialysis membrane placed above the Caco-2 monolayers. During the digestion process iron is released from the food matrix. Solubilized iron can diffused through the member and be taken up by the cells. Thus, in response to higher intracellular iron concentrations, Caco-2 cells forms ferritin. The formation of ferritin is quantified as an indicator of iron uptake by the cells. In our assays ferritin was measured by immunoassay in harvested Caco-2 cell 18 hours after the digestion. The total protein content of the cells was measured using BCA protein assay to allow a normalization of the results. To ensure the robustness of the results, three experiments were performed on separate days using cells from the same batch with three replicates each day. For each separate day, a mean±SD (n=3) for each samples was calculated and expressed by ng of ferritin/mg of protein. Then, to evaluate the impact of the recipe on iron bioaccessibility a percentage of difference was determined for each prototype against the two reference samples. Data (% of difference) collected for a same product were pooled and are reported as mean±SD in Figures below. Enzymes and buffers were used as blank (negative control). A solution of soluble iron chloride ($FeCl_3$) (6 μg/ml) with and without ascorbic acid, and an internal control were used as positive control. For the each experiments, reference samples and prototypes were fortified at a level of 8.4 mg of Fe/100 g of dry product with iron sulfate and a molar ratio of ascorbic acid to Iron (Fe) of 2:1. Iron bioaccessibility from intrinsic iron (i.e. samples without added iron) was also analyzed for iron bioaccessibility. Before the digestion steps, samples were reconstituted with the same quantity of hot water. The composition of references and prototypes is reported in Table 1 (sample containing milk) and Table 2 (samples without milk).

All the flours used to produce references and prototypes, as well as all the references and the prototypes were analyzed for their intrinsic iron and total phytic acid content. Iron was measured by ICP-MS. Total phytic acid concentrations was measured with a Megazyme Kit. Molar ratio of phytic acid (PA) to Fe was calculated from phytic acid values measured in flour and considering intrinsic and added iron in the recipes.

TABLE 1

Figure 2:
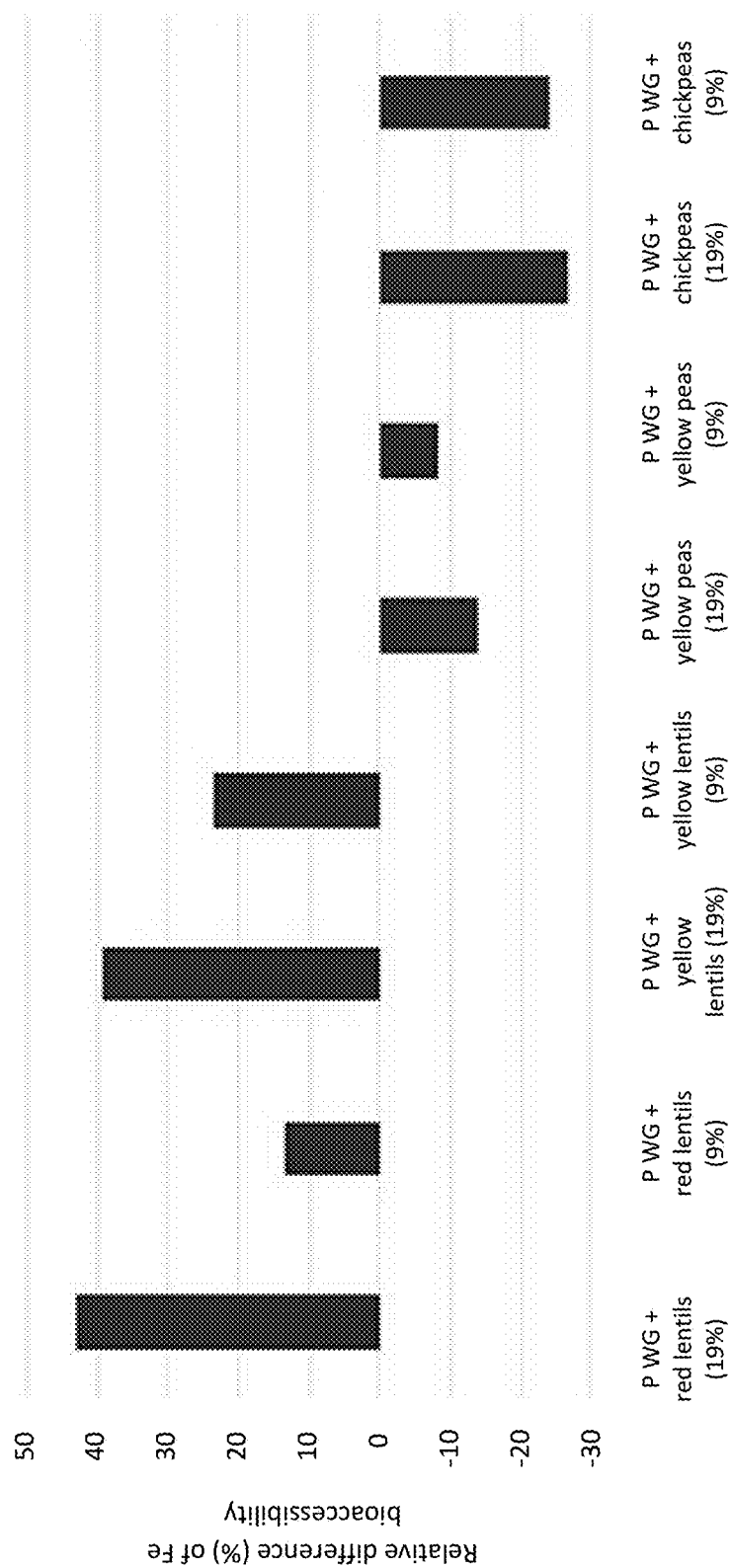
FIG. 2 Shows the effect of the addition of different legumes inc. lentils in recipes comprising wheat whole grain and milk on iron bio-accessibility. Reported percentage (mean±SD) represent the difference (%) in iron bio-accessibility between the samples and the reference comprising whole grains and milk only. All samples were fortified with the same level of iron and ascorbic acid.
Figure 3:
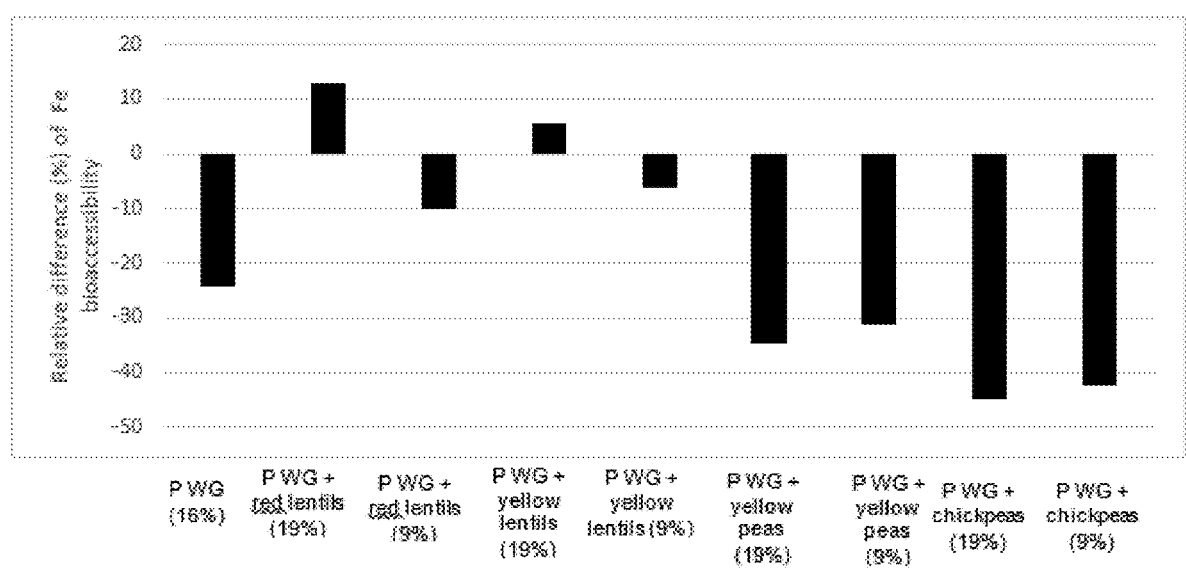
FIG. 3. Shows the effect of the addition of different legumes inc. lentils in recipes comprising wheat whole grain and milk on iron bio-accessibility. Reported percentage (mean±SD) represent the difference (%) in iron bio-accessibility between the sample and the reference containing refined flour and milk only.

Composition of references and prototypes samples (results presented in FIGS. 1 to 3)

| Samples | Refined wheat flour (%) | Skim milk (%) | Whole grains (%) | Legumes (%) | Malto-Dextrin | Fibres |
|---|---|---|---|---|---|---|
| Reference with refined flour | 49.6 | 24.1 | — | — | 6.9 | — |
| Reference with wheat (whole grains) | 33.6 | 24.1 | 16.8 | — | — | 4.5 |
| Prototypes wheat (whole grain) with 9.6% legumes (i.e. either red or yellow lentils, chickpea, pea) | 31.7 | 17.9 | 16.8 | 9.6 | — | 4.5 |
| Prototypes wheat (whole grains) with 19.1% legumes (i.e. either red lentils, yellow lentils, chickpea or, pea) | 26.4 | 12.6 | 16.8 | 19.1 | — | 4.5 |

TABLE 2

Figure 4:
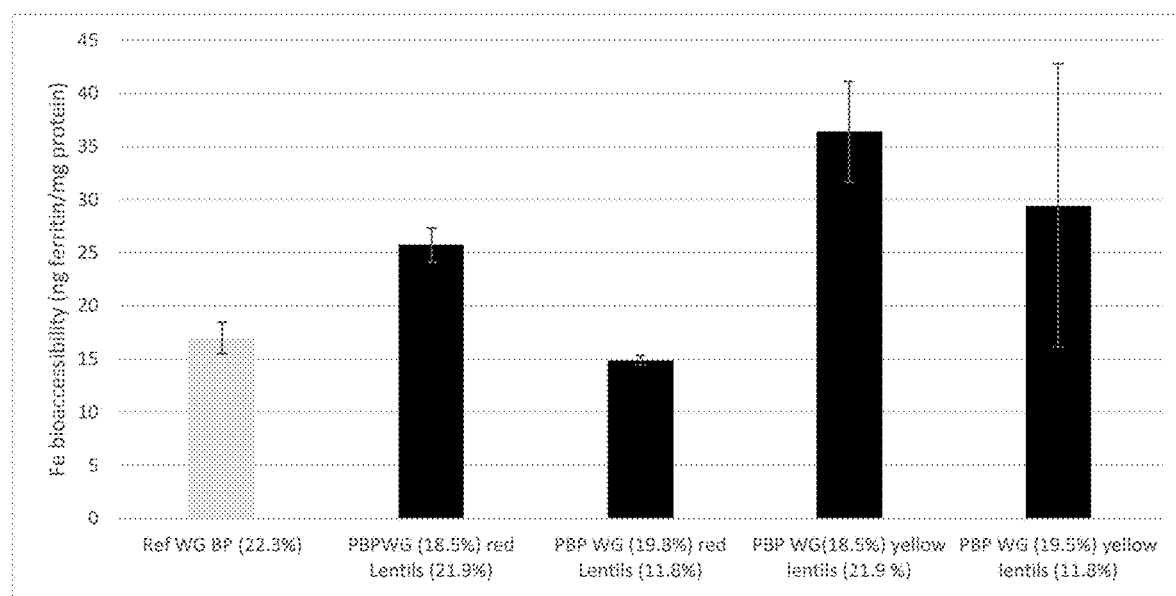
FIG. 4. Shows the effect of the addition of lentils on Fe bioaccessibility in a recipe comprising wheat whole grain.
Figure 5:
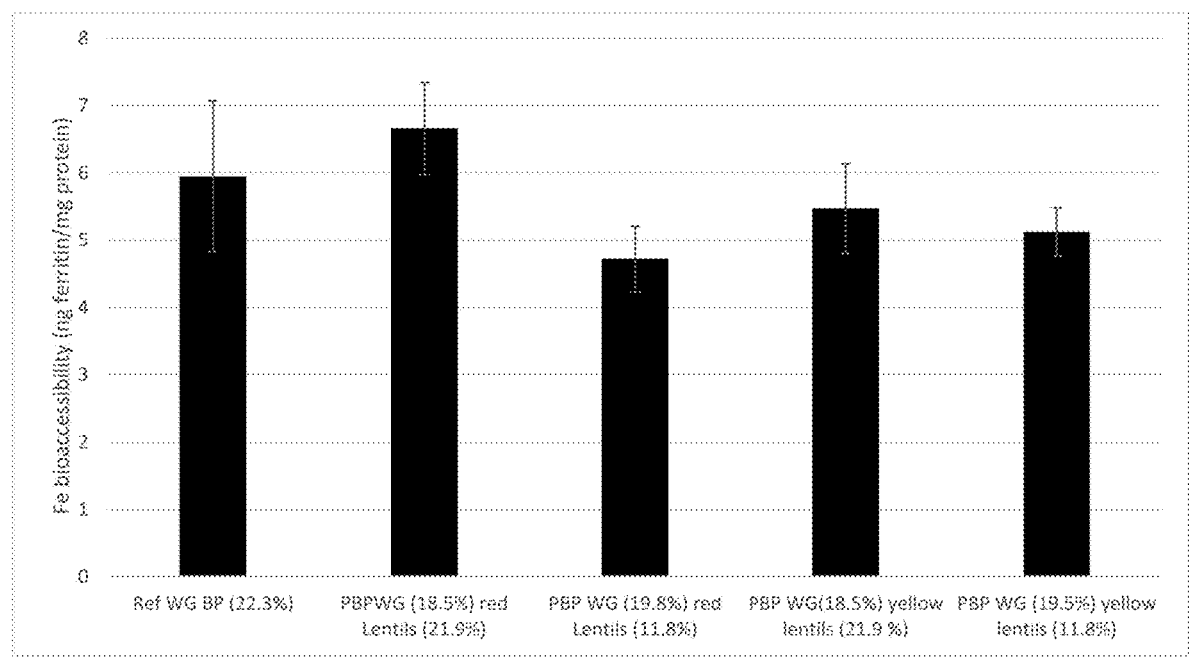
FIG. 5. Shows Fe bioaccessibility of intrinsic Fe from a reference comprising whole grain (ref WG BP) and from prototypes containing whole grains (WG) and lentils.

The composition of references and prototypes used to show the effect lentils on iron bioaccessibility in recipes containing refined flour and wheat whole grain (results presented on FIGS. 4 and 5).

| Samples | Refined wheat flour (%) | Skim milk (%) | Whole grains (%) | Legumes (%) | Fibers |
|---|---|---|---|---|---|
| Reference with wheat (whole grains) | 44.5 | — | 22.3 | — | 5.5 |
| Prototypes wheat (whole grain) with 11.6% legumes (i.e. either red or yellow lentils) | 38.6 | — | 19.8 | 11.6 | 5.2 |
| Prototypes wheat (whole grains) with 19.1% legumes red or yellow lentils) | 30.2 | — | 18.5 | 21.7 | 5.2 |

Results:

The iron and total phytic acid content of tested samples is reported in Table1. Results of the second set of samples (i.e. without milk) are presented on FIGS. 4 and 5.

TABLE 2

Iron (Fe), total phytic acid (PA) concentration as determined in the tested samples (containing whole grain and milk), and calculated molar ratio of PA to Fe.

| | Intrinsic Iron | | Phytic Acid | | Calculated molar ratio |
|---|---|---|---|---|---|
| | mg/100 g | ±SD | g/100 g | ±SD | of PA to Fe |
| Wheat flour (Whole grains) | 2.80 | (0.40) | 0.752 | (0.011) | |
| Wheat flour (refined) | 0.93 | (0.18) | 0.159 | (0.000) | |
| Yellow lentils flour | 6.55 | (0.17) | 0.974 | (0.008) | |
| Red lentils flour | 6.98 | (0.18) | 0.861 | (0.024) | |
| Chickpea flour | 4.83 | (0.84) | 0.966 | (0.009) | |
| Pea flour | 5.03 | (6.25) | 0.832 | (0.003) | |
| Reference refined flour | 0.52 | (0.15) | | | 0.7 |
| Reference wheat WG | 0.81 | (0.35) | | | 1.6 |

TABLE 2-continued

Iron (Fe), total phytic acid (PA) concentration as determined in the tested samples (containing whole grain and milk), and calculated molar ratio of PA to Fe.

| | Intrinsic Iron | | Phytic Acid | | Calculated molar ratio |
|---|---|---|---|---|---|
| | mg/100 g | ±SD | g/100 g | ±SD | of PA to Fe |
| Prototype red lentils (19%) | 2.14 | (0.22) | | | 2.6 |
| Prototype red lentils (9%) | 1.50 | (0.53) | | | 2.2 |
| Prototype chickpea (19%) | 1.89 | (0.27) | | | 2.9 |
| Prototype chickpea (9%) | 1.34 | (0.40) | | | 2.3 |
| Prototype yellow pea (19%) | 1.67 | (0.12) | | | 2.7 |
| Prototype yellow pea (9%) | 1.28 | (0.11) | | | 2.2 |
| Prototype yellow lentil (19%) | 2.07 | (0.25) | | | 2.8 |
| Prototype yellow lentil (9%) | 1.46 | (0.19) | | | 2.3 |

Results of the iron bioavailability tests of samples containing whole grains and milk are shown in FIGS. 1 to 3.

As can been seen from the results shown in FIG. 1; despite higher level of intrinsic iron in prototypes containing legumes when compared to reference samples iron, bioaccessibility was found to be in a similar range included between 10 and 22 ng ferritin/mg protein. Highest iron bioaccessibility from intrinsic iron was found for prototypes containing chickpea and red lentils, while the lowest values were found for prototypes containing yellow lentils (<10 ngferritin/mg protein).

As can be seen from the results shown in FIG. 2; after addition of iron as fortificant, despite an increased molar ratio of PA to Fe, the addition of yellow lentils (in replacement of milk and part of the refined flour) increased iron bioaccessibility from intrinsic and added iron when compared to the reference containing whole grains (molar ratio of PA to Fe=1.9). The same effect is found for red lentils. These results were not expected, and cannot be attributed to the level of intrinsic iron as depicted by FIG. 1. It can neither be attributed to the process since an opposite effect was observed for prototypes containing yellow pea and chickpea. As can be seen from the results shown in FIG. 3; the addition of yellow lentils and red lentils (19%) in a recipe containing wheat whole grains restore iron bioaccessibility to the same level of the recipe containing only refined flour (molar ratio of 0.7), this despite an increased molar ratio of PA to Fe. Recipe containing red lentil at 9% showed not additional effect when compared to the reference containing whole grains (PWG) (molar ratio 1.9), despite an increase level of phytic acid. This effect was not observed with the other legumes (i.e. yellow pea and chickpea) and was unexpected.

Results of the iron bioavailability tests performed with samples containing whole grains (without milk) are shown in FIGS. 4 to 5.

FIG. 4 shows that while the molar ratio of PA to Fe increases (in comparison to the reference containing only whole grain), iron bioaccessibility increases when lentils were added in the recipe. The experiment was performed with the same level of added iron and ascorbic acid. These effects cannot be attributed to the level of intrinsic iron as depicted by FIG. 5.

FIG. 5 shows that while the level of intrinsic iron in prototypes containing lentils is higher than in the reference, the iron bioaccessibility from prototypes containing lentils is similar or lower than from the reference sample (Ref WG BP).

Ref: Glahn R P, Lee O A, Yeung A, Goldman M I, Miller D D. Caco-2 cell ferritin formation predicts nonradiolabeled food iron availability in an in vitro digestion/Caco-2 cell culture model. J Nutr. 1998 September; 128(9):1555-61.

Example 2

Example of Infant Cereal Product Prepared with Water (% Weight).

A traditional infant cereal product to be reconstituted in water is prepared according to the following recipe: Wheat flour 35%, skim milk 17%, oil 7%, glucose 6%, sucrose 15%, vitamin and minerals 1% (including ferrous fumarate wherein said ferrous fumarate concentration equates to 1.6 mg per 100 Kcal) and, Yellow lentil flour 19%.

Example 3

Example of Infant Cereal Prepared with Milk (% Weight).

A traditional infant cereal product to be reconstituted in milk is prepared according to the following recipe: Rice flour 67%(71 g CHO), glucose 7%, sucrose 15%, banana 2% (1.4 g CHO), vitamin and minerals 1% (including ferrous fumarate wherein said ferrous fumarate concentration equates to 1.6 mg per 100 Kcal) and, red lentils flour 8%.

Example 4

An infant cereal product according to the present invention may be prepared according to the following recipe by using methods known to the person skilled in the art: Rice flour 60% (62.5 g CHO), sucrose 2%, galactose 20% banana 4% (1.4 g CHO), fat 5%, fiber 2.0%, vitamin and minerals 1% (including ferrous fumarate wherein said ferrous fumarate concentration equates to 1.6 mg per 100 Kcal) and, red lentils flour 16%.

The invention claimed is:

1. A method of maintaining or optimizing an iron status of an infant or child in need thereof, the method comprising administering to the infant or child a composition comprising non-haem iron, wholegrain, and a lentil product selected from the group consisting of a yellow lentil product, a red lentil product, and a combination thereof.

2. The method of claim 1, wherein the composition is an infant cereal or a nutritional composition.

3. The method of claim 1, wherein the non-haem iron is in the form of a physiologically acceptable iron chelate.

4. The method of claim 1, wherein the lentil product is in the form of dehulled whole lentils, dehulled crushed lentils, dehulled lentil flour, and combinations thereof.

5. The method of claim 1, wherein the composition comprises 5 to 70% of the lentil product.

6. The method of claim 1, wherein the composition comprises 5 to 30% of the wholegrain.

7. The method of claim 1, wherein the composition comprises 5 to 30% of the wholegrain, at least 1.6 mg/100 kcal of the non-haem iron, and 5 to 20% of the lentil product.

8. The method of claim 1, wherein the wholegrain is selected from the group consisting of wholegrain maize, wheat, rice, oat, corn, barley, rye, semolina, and combinations thereof.

9. A method of increasing the-bioavailability of non-haem iron in a composition comprising non-haem iron, wholegrain, and an anti-nutritional factor, the method comprising adding to the composition a lentil product selected from the group consisting of a yellow lentil product, a red lentil product, and a combination thereof.

10. The method of claim 9, wherein the anti-nutritional factor is phytic acid.

11. The method of claim 10, wherein the phytic acid is selected from the group consisting of myo-inositol phosphate (InsP), myo-inositol bisphosphate (InsP2), myoinositol triphosphate (InsP3), myo-inositol tetrakisphosphate (InsP4), myo-inositol pentakisphosphate (InsPS), myo-inositol hexakisphosphate (InsP6), and combinations thereof.

12. The method of claim 9, wherein the non-haem iron is in the form of a physiologically acceptable iron chelate.

13. The method of claim 9, wherein the wholegrain is selected from the group consisting of whole grain maize, wheat, rice, oat, corn, barley, rye, semolina, and a combination of any of the foregoing.

14. The method of claim 9, wherein the non-haem iron is selected from the group consisting of ferrous sulfate, ferrous bisglycinate, ferrous fumarate, and combinationa thereof.

15. The method of claim 9, wherein the lentil product is in the form of dehulled whole lentils, dehulled crushed lentils, dehulled lentil flour, and combinations thereof.

16. A method of treatment or prevention of suboptimal iron levels in an infant or a child in need thereof, the method comprising administering to the infant or child a composition comprising non-haem iron, wholegrain, and a lentil product selected from the group consisting of a yellow lentil product, a red lentil product, and a combination thereof.

* * * * *